United States Patent [19]

Sakano et al.

[11] Patent Number: 4,501,750
[45] Date of Patent: Feb. 26, 1985

[54] THIAZOLE COMPOUNDS, A PROCESS FOR PREPARING SAME AND A PHARMACEUTICAL COMPOSITION CONTAINING THE THIAZOLE COMPOUNDS

[75] Inventors: Isao Sakano; Tatsuro Yokoyama; Seitaro Kajiya, all of Yokohama; Yutaka Okazaki, Mobara; Hiroshi Tokuda, Mobara; Hiroshi Kawazura, Mobara; Mikio Kumakura, Mobara; Takuo Nakano; Akira Awaya, both of Yokohama, all of Japan

[73] Assignee: Mitsui Toatsu Kaguku Kabushiki Kaisha, Tokyo, Japan

[21] Appl. No.: 420,257
[22] PCT Filed: Jan. 13, 1982
[86] PCT No.: PCT/JP82/00012
§ 371 Date: Sep. 13, 1982
§ 102(e) Date: Sep. 13, 1982
[87] PCT Pub. No.: WO82/02383
PCT Pub. Date: Jul. 22, 1982

[30] Foreign Application Priority Data

Jan. 13, 1981 [JP] Japan .................................. 56-2741
Jan. 21, 1981 [JP] Japan .................................. 56-6231

[51] Int. Cl.$^3$ .................. A01K 31/425; C07D 417/12
[52] U.S. Cl. .................................. 514/369; 548/185; 548/195; 514/371; 514/825
[58] Field of Search ................. 548/195, 185; 424/270

[56] References Cited

U.S. PATENT DOCUMENTS 3,749,775  7/1973  Fancher .............................. 424/200

OTHER PUBLICATIONS

Gaugin et al., Pharmazie, 27, 164 (1972).
March, Advanced Org. Chem., pp. 382-383 (1977).

Primary Examiner—Robert Gerstl
Attorney, Agent, or Firm—Birch, Stewart, Kolasch & Birch

[57] ABSTRACT

The present invention provides new thiazole compounds possessing immuno-modulating activity, i.e. thiazole compounds of the general formula (1):

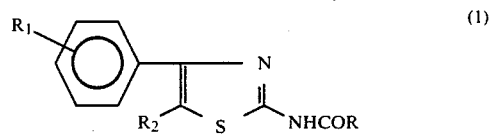

(1)

wherein $R_1$ stands for a hydrogen or halogen atom or a lower alkyl, lower alkoxy, substituted or unsubstituted phenoxy, nitro or cyano group, $R_2$ for a hydrogen atom or a lower alkyl or lower alkylthio group, and R for an α-halogenoalkyl group or the grouping:

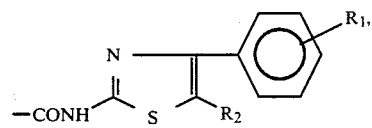

a process for preparing same and pharmaceutical compositions containing the thiazole compounds.

More particularly, the present invention provides new thiazole compounds of the above general formula (1) which have immuno-modulating activity and are thus effective against immunodiseases such as chronic rheumatoid arthritis and also useful against viral diseases or for the immunotherapy of cancers, but show weak toxicity and are thus extremely desirous as medicines, a process for the preparation of the thiazole compounds and pharmaceutical compositions containing the thiazole compounds.

9 Claims, No Drawings

THIAZOLE COMPOUNDS, A PROCESS FOR PREPARING SAME AND A PHARMACEUTICAL COMPOSITION CONTAINING THE THIAZOLE COMPOUNDS

FIELD OF THE INVENTION

The present invention relates to new thiazole compounds which have immuno-modulating activity and are thus effective against immunodiseases such as chronic rheumatoid arthritis and also useful against viral diseases or for the immunotherapy of cancers, a process for preparing the compounds and medicinal compositions containing same.

A number of steroid-type and nonsteroid-type antiinflammatory drugs have heretofore been clinically employed against autoimmune diseases such as rheumatism. However, these drugs are not quite satisfactory in their pharmacological effects, side effects and toxicity. The present inventors have carried out an extensive research on chemical substances, which give a peculiar effect to cells that take part in an immunity response and act to modulate the immunity response of the host. As a result, they have succeeded in obtaining thiazole derivatives which are extremely desirous as medicines having excellent immuno-modulating activity but little toxicity.

DISCLOSURE OF INVENTION

The present invention relates to thiazole compounds of the general formula (1):

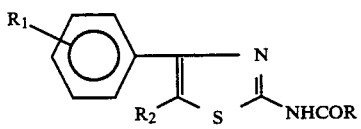

wherein $R_1$ stands for a hydrogen or halogen atom or a lower alkyl, lower alkoxy, substituted or unsubstituted phenoxy, nitro or cyano group, $R_2$ for a hydrogen atom or a lower alkyl or lower alkylthio group, and R for an α-halogenoalkyl group or the grouping:

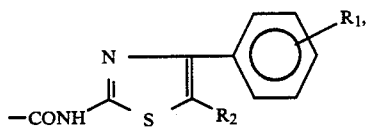

a process for preparing same and pharmaceutical compositions containing the thiazole compounds.

More particularly, the present invention provides the new thiazole compounds of the above general formula (1), which have immuno-modulating activity and are thus effective against immunodiseases such as chronic rheumatoid arthritis and also useful against viral diseases or for the immunotherapy of cancers, but show weak toxicity and are thus extremely desirous as medicines, a process for preparing the thiazole compounds and medicinal compositions containing the thiazole compounds.

The compounds concerned with the present invention represented by the general formula (1) show tautomerism between their amine-form and their imine-form. Thus, the compounds of the present invention include all of these tautomers.

Illustrative of the representative compounds of the present invention are as follows:
N,N'-bis(4-phenylthiazol-2-yl)oxamide;
N,N'-bis[4-(p-chlorophenyl)thiazol-2-yl]oxamide;
N,N'-bis[4-(m-chlorophenyl)thiazol-2-yl]oxamide;
N,N'-bis[4-(o-chlorophenyl)thiazol-2-yl]oxamide;
N,N'-bis[4-(p-bromophenyl)thiazol-2-yl]oxamide;
N,N'-bis[4-(m-bromophenyl)thiazol-2-yl]oxamide;
N,N'-bis[4-(o-bromophenyl)thiazol-2-yl]oxamide;
N,N'-bis[4-(p-methylphenyl)thiazol-2-yl]oxamide;
N,N'-bis[4-(m-methylphenyl)thiazol-2-yl]oxamide;
N,N'-bis[4-(o-methylphenyl)thiazol-2-yl]oxamide;
N,N'-bis[4-(p-methoxyphenyl)thiazol-2-yl]oxamide;
N,N'-bis[4-(m-methoxyphenyl)thiazol-2-yl]oxamide;
N,N'-bis[4-(o-methoxyphenyl)thiazol-2-yl]oxamide;
N,N'-bis[4-(p-phenoxyphenyl)thiazol-2-yl]oxamide;
N,N'-bis[4-(p-(4-chlorophenoxy)phenyl)-5-methylthiazol-2-yl]oxamide;
N,N'-bis 4-(p-nitrophenyl)thiazol-2-yl oxamide;
N,N'-bis 4-(m-nitrophenyl)thiazol-2-yl oxamide;
N,N'-bis 4-(o-nitrophenyl)thiazol-B 2-yl oxamide;
N,N'-bis 4-(p-cyanophenyl)thiazol-2-yl oxamide;
N,N'-bis 4-(m-cyanophenyl)thiazol-2-yl oxamide;
N,N'-bis 4-(o-cyanophenyl)thiazol-2-yl oxamide;
N,N'-bis(5-methylthio-4-phenylthiazol-2-yl)oxamide;
2-(α-chloropropionylamino)-4-phenylthiazole;
2-(α-bromopropionylamino)-4-phenylthiazole;
2-(α-chloro-n-butylylamino)-4-phenylthiazole;
2-α-bromo-n-butylylamino)-4-phenylthiazole;
2-(α-chloro-α-methylpropionylamino)-4-phenylthiazole;
2-(α-bromo-α-methylpropionylamino)-4-phenylthiazole; and
2-(α-chlorohexylylamino)-4-phenylthiazole.

The compounds of the present invention represented by the general formula (1) can be prepared by reacting a 2-aminothiazole represented by the general formula:

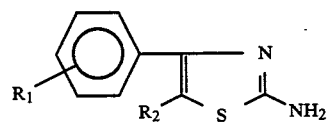

wherein $R_1$ and $R_2$ have the same definitions as given above, with halide of the general formula (3):

$$R_3—CO—X \qquad (3)$$

wherein $R_3$ stands for an α-halogenoalkyl group or X—CO— and X stands for a halogen atom.

The reaction may be carried out by either dissolving or suspending a starting material represented by the general formula (2) (which may optionally be in the form of a suitable acid-addition salt) in a solvent and then adding dropwise or in a similar manner halide of the general formula (3) to the solution or suspension. The reactants may sufficiently be used generally in stoichiometrically calculated amounts.

As suitable solvents to be used for the reaction may be mentioned, for example, benzene, toluene, xylene, acetone, ethyl methyl ketone, dioxane, 1,2-dimethoxyethane, tetrahydrofuran and N,N-dimethylformamide. For the sake of removing hydrogen chloride which will be produced in the course of the reaction, it may be possible to use an organic base such as pyridine or triethylamine or an inorganic base such as sodium carbonate, potassium carbonate or sodium hydrogen carbonate. The above reaction may proceed at temperatures below room temperature. However, it is possible to heat the reaction mixture to a temperature up to the boiling point of the solvent so as to accelerate the reaction.

Most of the 2-amino-4-phenylthiazoles, the starting materials, represented by the general formula (2) are known compounds. They are described in detail, for example, in technical publications [Jacques V. Metzger, ed. "The Chemistry of Heterocyclic Compounds", Vol. 34; "Thiazole and Its Derivatives", Part Two, (1979)].

The compounds of the present invention represented by the general formula (1) have pharmacological activity. It is of particular worth to mention that these compounds have excellent immuno-modulating activity. Since their toxicity is low, they are extremely useful as medicines.

The pharmacological activity of the compounds of the present invention was confirmed as follows: Various test systems using animals have been routinely adopted for the determination of immunomodulating activity. Results of reinforcement tests of the delayed hypersensitivity, which are considered to be the most representative ones among such known test systems, will hereinafter be described as follows:

The delayed hypersensitivity induced on a mouse when picryl chloride(2-chloro-1,3,5-trinitrobenzene) is coated on the skin of the mouse is known as a typical cellular immunity. This is one of the test systems commonly adopted throughout the world [see Asherson, G. L. and Ptak, W. "Contact and Delayed Hypersensitivity in the Mouse—I. Active Sensitization and Passive Transfer", Immunology, 15, 405–416 (1968)].

The above test system was used for the reinforcement tests of the delayed hypersensitivity.

TEST EXAMPLE 1

Reinforcement Test of Delayed Hypersensitivity

Test Procedures:

Groups of eight ICR male mice, each having a body weight of about 30 g, were used for the test.

Sensitization was effected by coating a 3% solution of picryl chloride in a 4/1 mixture of olive oil and acetone on the shaved abdomen of each of the mice.

Simultaneously with the sensitization, a solution or suspension of a compound of the present invention dissolved or suspended in a 0.2% solution of carboxymethylcellulose in a physiological saline was orally administered to the mouse at a dose of 50 mg per Kg of its body weight. To each mouse of a control group, a 0.2% carboxymethylcellulose solution was similarly administered in a physiological saline.

The delayed hypersensitivity was induced 7 days after the sensitization by pinching each of the pinnae of each mouse with a pair of forceps whose tip portions were wrapped with a felt impregnated with a 1% solution of picryl chloride in olive oil and coating the pinnae with the solution. The thickness of each pinna was measured before the challenging and 24 hours after the challenging and the ratio of increase of the thickness (average value of both of the pinnae of the eight mice) is shown in Table 1.

For comparison, a similar test was carried out using Levamisole hydrochloride. Its results are also shown.

F.t tests were carried out on the thus-obtained test results. Any group in which the test results were superior to those of the control group at significance levels of $P<0.05$ and $P<0.01$ are marked, respectively, by an asterisk(*) and double asterisks(**).

Results:

When the compounds of the present invention were administered simultaneously with sensitization, the delayed hypersensitivity caused by a challenging was reinforced. The reinforcement effect of such compounds was recognized to be comparative with or higher than that attained by Levamisole which was used for the sake of comparison.

Thus, the compounds of the present invention are considered to have an effect of modulating the cellular immunity response (immuno-modulating activity) in mice.

TABLE 1

Reinforcement Tests of Delayed Hypersensitivity

| Compound to be tested (shown by formula) | Ratio of Increase of Pinna Thickness (%) |
|---|---|
| 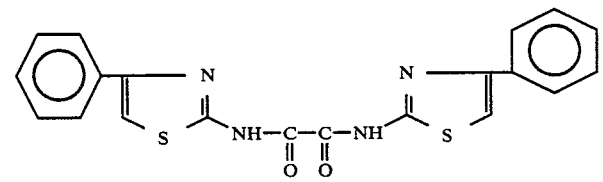 | 30.3 |
| 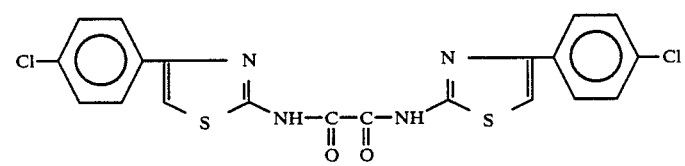 | 29.5 |

TABLE 1-continued

Reinforcement Tests of Delayed Hypersensitivity

| Compound to be tested (shown by formula) | Ratio of Increase of Pinna Thickness (%) |
|---|---|
| CH₃O-C₆H₄-CH=C(S-)-C(=N-)-NH-CO-CO-NH-(=N-)C(-S)-CH=C₆H₄-OCH₃ | 36.5** |
| CH₃S-C(=CH-C₆H₅)-S-C(=N-)-NH-CO-CO-NH-(=N-)C-S-(C₆H₅-CH=)C-SCH₃ | 27.3 |
| C₆H₅-CH=C(S-)-C(=N-)-NHCOCHClCH₃ | 36.1* |
| C₆H₅-CH=C(S-)-C(=N-)-NHCOCHBrCH₃ | 32.9 |
| Levamisole·HCl | 31.2* |

The adjuvant arthritis in rats caused by the injection of a *Mycobacterium tuberculosis* adjuvant is often utilized for a model test of chronic rheumatoid arthritis in human.

The mechanism of manifestation of this disease has not completely been elucidated, but it is known that the cellular immunity plays an important role. The immuno-modulating activity of the compounds of the present invention was investigated in accordance with this known adjuvant arthritis test.

TEST EXAMPLE 2

Ajuvant Arthritis Test (Table 2)

Test Procedures:

8-Week-old SD male rats were used for the test. In 0.1 ml of fluid paraffin, 0.4 mg of dry-dead cells of *Mycobacterium tuberculosis* were suspended, and the suspension was injected under the heel skin of the right hind leg of each rat. Each of the compounds of the present invention was subcutaneously administered 9 times in total before and after the injection of the adjuvant. Each of the compounds of the present invention was dissolved or suspended in a 0.2% solution of carboxymethylcellulose in physiological saline and administered to each rat at a dose of 5 mg per Kg of the body weight. The swollen volume of the left hind leg was measured during the period of from the day of injection to the day of completion of the test, and the swelling ratio was calculated. For comparison, a similar test was conducted using Levamisole hydrochloride. F.t tests were carried out on the test results obtained. Any group in which the test results were superior to those of a control group administered with a 0.2% solution of carboxymethylcellulose in physiological saline at significance levels of $P<0.05$ and $P<0.01$ are marked, respectively, by an asterisk(*) and double asterisks(**).

Results:

The secondary inflammation of the adjuvant arthritis was remarkably suppressed by the compounds of the present invention. Their effects were statistically significant over the control group. It was recognized that they exhibited an activity comparative with or stronger than that of Levamisole, which was used for comparison. Thus, the compounds of the present invention are considered to have immuno-modulating activity and anti-arthritic activity.

TABLE 2

| Compound to be tested (shown by formula) | Number of cases | Swell suppression ratio to control group (%) (average value from 16th to 20th days |
|---|---|---|
| [phenyl-thiazole]-NH-C(=O)-C(=O)-NH-[thiazole-phenyl] | 10 | 51.0** |
| Cl-[phenyl-thiazole]-NH-C(=O)-C(=O)-NH-[thiazole-phenyl]-Cl | 10 | 51.9* |
| $CH_3O$-[phenyl-thiazole]-NH-C(=O)-C(=O)-NH-[thiazole-phenyl]-$OCH_3$ | 10 | 14.1 |
| [phenyl($CH_3S$)-thiazole]-NH-C(=O)-C(=O)-NH-[thiazole-phenyl($SCH_3$)] | 10 | 35.5* |
| [phenyl-thiazole]-NHCOCHCH$_3$ (Cl) | 10 | 12.1 |
| [phenyl-thiazole]-NHCOCHCH$_3$ (Br) | 10 | 20.0* |
| Levamisole.HCl | 44 | 19.8* |

As illustrated in Test Examples 1 and 2, the compounds of the present invention have excellent immunomodulating effect. Thus, they are effective for the remedy of diseases accompanied notably by reduction or abnormal change of immune functions, for example, autoimmune diseases such as chronic rheumatoid arthritis.

A toxicity test on the effective ingredient of certain medicines according to this invention will now be described below as Test Example 3.

TEST EXAMPLE 3

Acute Toxicity Test through Oral Administration

Test Procedures:

To each of a group of five ddY male mice, was orally administered a medicine dissolved or suspended in physiological saline. They were observed for 7 days after the administration and an estimated $LD_{50}$ value was obtained.

Results:

The estimated $LD_{50}$ value of the effective ingredient of a medicine according to this invention was 1,000 mg/kg or higher. This value is far greater than the estimated $LD_{50}$ value of Levamisole.HCl, the latter value ranging 200–300 mg/Kg. Therefore, the toxicity of the compound of the present invention is considered to be low.

The compound of this invention may be used in the form of a free base as a raw material for preparing a medicinal composition. However, it is also possible to use the compound as a pharmaceutically acceptable salt thereof.

The medicine according to this invention may be administered in the same preparation form and by the same administration method as conventional immuno-modulating agents and carcinostatic substances. For instance, as an orally administrable preparation, it may be used in the form of capsules, granules, pills, fine grains, tablets or syrup. For administering through the rectum, it is suitable to prepare the medicine into suppositories. For injection, it may be applied subcutaneously, intramuscularly or intravenously.

As diseases to which an immuno-modulating activity of the new compounds of this invention can be applied, there may be mentioned diseases accompanied by an abnormal change of immune functions, for example, chronic rheumatoid arthritis; autoimmune diseases such as polymyositis; various infectious diseases; and a wide variety of cancers. It is expected that the immuno-modulating agent of the present invention would normalize the immune functions of patients affected by such diseases.

It is desirous to choose a suitable administration method and an appropriate preparation form for using the new compounds of the present invention as a medicine depending on the type of disease and conditions of each patient. In case of oral administration, the dose of a compound of the present invention is 0.5 to 100 mg, preferably 1 to 30 mg per Kg of the body weight per day. In case of administering to the rectum, the dose is suitably 1 to 100 mg per Kg of the body weight per day, while, in case of intravenous administration, the dose is preferably 1 to 10 mg per Kg of the body weight per day. Where it is administered subcutaneously or intramuscularly, the dose of the compound of this invention is preferably 1 to 30 mg per Kg of the body weight per day. It is desirable that these doses be appropriatedly adjusted according to the type of diseases and the conditions of each patient. The therapeutic effect of the effective ingredient of the present invention may be increased, depending on the type of diseases and the conditions of a patient, by using other medicines in combination. For example, when chemotherapeutic agents for cancers, such as alkylating agents and antimelobolies, which have a side effect of reducing the immunizing capacity of patients, are administered, the manifestation of such side effect may be prevented and their therapeutic effect may be synergistically increased if the effective ingredient of the present invention is used in combination.

Examples of this invention will hereinafter be described.

EXAMPLE 1

In 80 ml of tetrahydrofuran was dissolved 17.6 g of 2-amino-4-phenylthiazole and 10.0 g of triethylamine. The solution was cooled to 5° C. Then, to the solution, was dropped a tetrahydrofuran solution containing 6.4 g of oxalyl chloride. After the completion of the dropwise addition, the solution mixture was stirred for 4 hours at room temperature. Deposited crystals were collected through filtration and then successively washed with water and then methanol. The resultant crystals were recrystallized from N,N-dimethylformamide to obtain 7.5 g of N,N'-bis(4-phenylthiazol-2-yl)oxamide.

Melting point: 292°–293° C.

| Elementary analysis values as $C_{20}H_{14}N_4O_2S_2$: | | | | |
|---|---|---|---|---|
| | C | H | N | S |
| Calcd. (%): | 59.10 | 3.47 | 13.78 | 15.78 |
| Found (%): | 58.97 | 3.43 | 13.81 | 15.51 |

IR($\nu_{max}^{KBr}$, cm$^{-1}$): 3440, 1690, 1555, 1480, 1435, 1330, 1280, 1080, 1070, 1035, 870, 860, 754, 705.

Following the procedures of Example 1, the compounds of the following Examples 2–12 were prepared from their corresponding starting compounds.

EXAMPLE 2

N,N'-bis[4-(p-chlorophenyl)thiazol-2-yl]oxamide

Melting lpoint: >300° C.

| Elementary analysis values: | | | | | |
|---|---|---|---|---|---|
| | C | H | Cl | N | S |
| Calcd. (%): | 50.53 | 2.54 | 14.92 | 11.78 | 13.49 |
| Found (%): | 50.71 | 2.51 | 15.01 | 11.98 | 13.30 |

IR($\nu_{max}^{KBr}$, cm$^{-1}$): 3370, 1685, 1540, 1425, 1095, 1015, 835, 745.

EXAMPLE 3

N,N'-bis[4-(m-chlorophenyl)thiazol-2-yl]oxamide

Melting point: 284°–287° C.

| Elementary analysis values: | | | | | |
|---|---|---|---|---|---|
| | C | H | Cl | N | S |
| Calcd. (%): | 50.53 | 2.54 | 14.92 | 11.78 | 13.49 |
| Found (%): | 50.39 | 2.49 | 15.01 | 11.57 | 13.40 |

IR($\nu_{max}^{KBr}$, cm$^{-1}$): 3240, 1703, 1663, 1602, 1555, 1540, 1435, 1315, 1285, 850, 845, 735.

EXAMPLE 4

N,N'-bis[4-(p-methylphenyl)thiazol-2-yl]oxamide

Melting point: >300° C.

| Elementary analysis values: | | | | |
|---|---|---|---|---|
| | C | H | N | S |
| Calcd. (%): | 60.81 | 4.18 | 12.89 | 14.76 |
| Found (%): | 61.04 | 4.09 | 13.00 | 14.87 |

IR($\nu_{max}^{KBr}$, cm$^{-1}$): 3380, 1695, 1535, 1490, 1435, 1330, 1305, 1280, 860, 830, 745, 740.

EXAMPLE 5

N,N'-bis[4-(p-methoxyphenyl)thiazol-2-yl]oxamide

Melting point: >300° C.

| Elementary analysis values: | | | | |
|---|---|---|---|---|
| | C | H | N | S |
| Calcd. (%): | 56.64 | 3.89 | 12.01 | 13.75 |
| Found (%): | 56.87 | 3.91 | 12.16 | 13.66 |

IR($\nu_{max}^{KBr}$, cm$^{-1}$): 3360, 1615, 1555, 1490, 1440, 1290, 1260, 1180, 1035, 890, 745.

EXAMPLE 6

N,N'-bis[4-(p-nitrophenyl)thiazol-2-yl]oxamide

Melting point: >300° C.

| | Elementary analysis values: | | | |
|---|---|---|---|---|
| | C | H | N | S |
| Calcd. (%): | 48.38 | 2.44 | 16.93 | 12.92 |
| Found (%): | 48.34 | 2.45 | 16.79 | 12.77 |

IR($\nu_{max}^{KBr}$, cm$^{-1}$): 3400, 1690, 1600, 1535, 1520, 1430, 1350, 1290, 1015, 850, 740.

EXAMPLE 7

N,N'-bis[4-(m-nitrophenyl)thiazol-2-yl]oxamide

Melting point: >300° C.

| | Elementary analysis values: | | | |
|---|---|---|---|---|
| | C | H | N | S |
| Calcd. (%): | 48.38 | 2.44 | 16.93 | 12.92 |
| Found (%): | 48.52 | 2.51 | 16.55 | 12.87 |

IR($\nu_{max}^{KBr}$, cm$^{-1}$): 3440, 1685, 1665, 1555, 1545, 1520, 1370, 1365, 1430, 1290, 860, 840, 740.

EXAMPLE 8

N,N'-bis[4-(p-cyanophenyl)thiazol-2-yl]oxamide

Melting point: >300° C.

| | Elementary analysis values: | | | |
|---|---|---|---|---|
| | C | H | N | S |
| Calcd. (%): | 57.88 | 2.65 | 18.41 | 14.05 |
| Found (%): | 57.78 | 2.58 | 17.99 | 13.98 |

IR($\nu_{max}^{KBr}$, cm$^{-1}$): 3440, 2250, 1755, 1620, 1540, 1505, 1325, 1300, 850, 820, 765.

EXAMPLE 9

N,N'-bis[4-(p-(4-chlorophenoxy)phenyl)-5-methyl-5-methylthiazol-2-yl]oxamide

Melting point: >300° C.

| | Elementary analysis values: | | | | |
|---|---|---|---|---|---|
| | C | H | Cl | N | S |
| Calcd. (%): | 59.39 | 3.52 | 9.31 | 8.15 | 9.33 |
| Found (%): | 59.12 | 3.45 | 9.61 | 8.06 | 9.55 |

IR($\nu_{max}^{KBr}$, cm$^{-1}$): 3330, 1695, 1550, 1545, 1490, 1440, 1280, 1265, 1250, 855, 825.

EXAMPLE 10

N,N'-bis[5-methylthio-4-phenylthiazol-2-yl]oxamide

Melting point: 274°-275° C.

| | Elementary analysis values: | | | |
|---|---|---|---|---|
| | C | H | N | S |
| Calcd. (%): | 52.99 | 3.64 | 11.24 | 25.72 |
| Found (%): | 52.95 | 3.55 | 11.17 | 25.55 |

IR($\nu_{max}^{KBr}$, cm$^{-1}$): 3200, 1680, 1525, 1410, 1300, 1275, 1130.

EXAMPLE 11

N,N'-bis[4-(m-methylphenyl)thiazol-2-yl]oxamide

Melting point: 260°-262° C.

| | Elementary analysis values: | | | |
|---|---|---|---|---|
| | C | H | N | S |
| Calcd. (%): | 60.81 | 4.18 | 12.89 | 14.76 |
| Found (%): | 60.72 | 4.08 | 13.00 | 14.71 |

IR($\nu_{max}^{KBr}$, cm$^{-1}$): 3220, 1700, 1660, 1550, 1530, 1440, 1320, 1280, 855, 840, 790, 730, 720.

EXAMPLE 12

N,N'-bis[4-(p-fluorophenyl)thiazol-2-yl]oxamide

Melting point: >300° C.

| | Elementary analysis values: | | | | |
|---|---|---|---|---|---|
| | C | H | F | N | S |
| Calcd. (%): | 54.29 | 2.73 | 8.59 | 12.66 | 14.49 |
| Found (%): | 54.39 | 2.79 | 8.61 | 12.67 | 14.45 |

IR($\nu_{max}^{KBr}$, cm$^{-1}$): 3360, 1690, 1545, 1540, 1485, 1428, 1275, 1225, 1160, 1060, 840, 750, 740.

EXAMPLE 13

Into 50 ml of acetone, were added 12.5 g of 2-amino-4-phenylthiazole and 7.0 g of triethylamine. The mixture was cooled to −10°−−20° C. To the mixture solution, 11.7 g of α-chloropropionylchloride was slowly dropped. After the completion of the dropwise addition, the resultant mixture solution was agitated at room temperature for 3 hours. Then, the reaction mixture was poured into 500 ml of water. Resulting oily substance was extracted with ethyl acetate. The extract was then successively washed with dilute hydrochloric acid and water. After drying the solution, the ethyl acetate was removed under reduced pressure. The residue was recrystallized from an ether/n-hexane mixed solvent to obtain 13.2 g of 2-(α-chloropropionylamino)-4-phenylthiazole.

Melting point: 98°-99° C.

| | Elementary analysis values as $C_{12}H_{11}ClN_2OS$: | | | | |
|---|---|---|---|---|---|
| | C | H | Cl | N | S |
| Calcd. (%): | 54.03 | 4.16 | 13.29 | 10.50 | 12.02 |
| Found (%): | 53.95 | 4.09 | 13.36 | 9.99 | 11.98 |

IR($\nu_{max}^{KBr}$, cm$^{-1}$): 3150, 2900, 1705, 1610, 1570, 1550, 1490, 1450, 1340, 1280, 1180, 1080, 1000, 910, 740, 700.

NMR($\delta_{TMS}^{CDCl_3}$, ppm): 1.70(3H, d, J=8.0 Hz), 4.40(1H, q, J=8.0 Hz), 7.16(1H, s), 7.3-7.9(5H, m), 10.45(1H, bs: disappeared with D$_2$O).

EXAMPLE 14

Into 50 ml of tetrahydrofuran, were added 3.5 g of 2-amino-4-phenylthiazole and 2.0 g of triethylamine. The mixture was cooled to 0°−−5° C. Then, 4.3 g of α-bromopropionylbromide was dropped to the solution mixture. After the completion of the dropwise addition, the solution mixture was stirred at room temperature for 1 hour. Then, the reaction mixture was concentrated under reduced pressure. The residue was taken up in chloroform and washed with water. Upon removal of chloroform, a crude reaction product was obtained. It was thereafter subjected to silica gel chromatography and then eluted with a chloroform/methyl alcohol (40:1) mixed solvent. It was then recrystallized from an ether/cyclohexane mixed solvent, thereby obtaining 4.2 g of 2-(α-bromopropionylamino)-4-phenylthiazole.

Melting point: 113.5°–115° C.

| Elementary analysis values as $C_{12}H_{11}BrN_2OS$: | | | | |
| --- | --- | --- | --- | --- |
| | C | H | Br | N | S |
| Calcd. (%): | 46.31 | 3.56 | 25.68 | 9.00 | 10.30 |
| Found (%): | 46.45 | 3.49 | 25.71 | 8.97 | 10.32 |

NMR($\delta_{TMS}^{CDCl_3}$, ppm): 1.72(3H, d, J=7.0 Hz), 4.24(1H, q, J=7.0 Hz), 7.18(1H, s), 7.4–7.9(5H, m), 12.1(1H, bs: disappeared with $D_2O$).

Following the procedures of Example 13 and 14, the compounds of the following Examples 15 and 16 were prepared.

EXAMPLE 15

2-(α-bromo-n-butyrylamino)-4-phenylthiazole

Melting point: 85°–86.5° C.

| Elementary analysis values as $C_{13}H_{13}BrN_2OS$: | | | | |
| --- | --- | --- | --- | --- |
| | C | H | Br | N | S |
| Calcd. (%): | 48.01 | 4.03 | 24.57 | 8.61 | 9.86 |
| Found (%): | 48.18 | 4.13 | 24.61 | 8.51 | 9.78 |

NMR($\delta_{TMS}^{CDCl_3}$, ppm): 0.64(3H, t, J=7.0 Hz), 1.84(2H, m), 3.72(1H, t, J=7.0 Hz), 7.13(1H, s), 7.3–7.84(5H, m)

EXAMPLE 16

2-(α-bromo-α-methylpropionylamino)-4-phenyl-thiazole

Melting point: 93.5°–94.5° C.

| Elementary analysis as $C_{13}H_{13}BrN_2OS$: | | | | |
| --- | --- | --- | --- | --- |
| | C | H | Br | N | S |
| Calcd. (%): | 48.01 | 4.03 | 24.57 | 8.61 | 9.86 |
| Found (%): | 47.99 | 3.96 | 24.67 | 8.59 | 9.87 |

NMR($\delta_{TMS}^{CDCl_3}$, ppm): 2.00(6H, s), 7.20(1H, s), 7.4–7.9(5H, m), 9.92(1H, bis: disappeared with $D_2O$).

The invention being thus described, it will be obvious that the same way be varied in many ways. Such variations are not to be regarded as a departure from the spirit and scope of the invention, and all such modifications as would be obvious to one skilled in the art are intended to be included within the scope of the following claims.

I claim:

1. A thiazole compound of the formula:

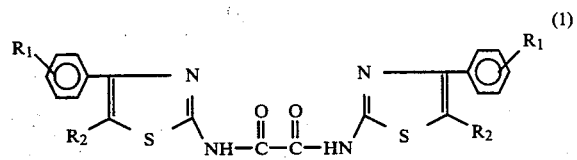

wherein $R_1$ is a member selected from the group consisting of hydrogen, chloro, bromo, methyl, methoxy, p-phenoxy, p-chlorophenoxy, nitro and cyano, and $R_2$ is a member selected from the group consisting of hydrogen, and methylthio.

2. A thiazole compound according to claim 1, wherein $R_1$ is hydrogen, chloro or methoxy and $R_2$ is hydrogen or methylthio.

3. A pharmaceutical composition possessing immunomodulating activity comprising at least one thiazole compound according to claim 1 as an active ingredient and a pharmaceutically acceptable carrier or diluent.

4. A pharmaceutical composition possessing immunomodulating activity comprising at least one thiazole compound according to claim 2 as an active ingredient and a pharmaceutically acceptable carrier or diluent.

5. A method for treating chronic rheumatoid arthritis comprising administering an effective anti-arthritic amount of a thiazole compound according to claim 1.

6. A method for treating chronic rheumatoid arthritis comprising administering an effective anti-arthritic amount of a thiazole compound according to claim 2.

7. A thiazole compound of the formula:

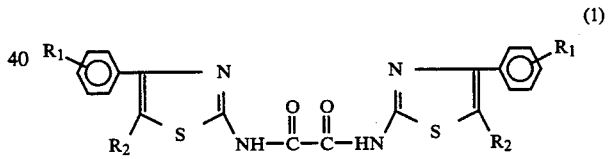

wherein $R_1$ stands for a hydrogen or halogen atom or a lower alkyl, lower alkoxy, p-chlorophenoxy, nitro or cyano group, and $R_2$ for a hydrogen atom or a lower alkyl or lower alkylthio group.

8. A pharmaceutical composition possessing immunomodulating activity comprising at least one thiazole compound according to claim 1 as an active ingredient and a pharmaceutically acceptable carrier or diluent.

9. A method for treating chronic rheumatoid arthritis comprising administering an effective anti-arthritic amount of a thiazole compound according to claim 1.

* * * * *

UNITED STATES PATENT AND TRADEMARK OFFICE
CERTIFICATE OF CORRECTION

PATENT NO. : 4,501,750

DATED : Feburary 26, 1985

INVENTOR(S) : Isao SAKANO et al

It is certified that error appears in the above-identified patent and that said Letters Patent is hereby corrected as shown below:

On the title page;

In section[30], change:

"Jan. 21,1981 [JP]   Japan...........56-6231"to

--Jan. 21, 1981 [JP]   Japan..........56-6321--

Signed and Sealed this

Sixth Day of August 1985

[SEAL]

*Attest:*

DONALD J. QUIGG

*Attesting Officer*   *Acting Commissioner of Patents and Trademarks*